United States Patent [19]

Travers et al.

[11] Patent Number: 5,464,869
[45] Date of Patent: Nov. 7, 1995

[54] USE OF DIMERCAPTAN ACIDS, SALTS AND METABOLITES THEREOF AS ANTIRETROVIRAL TREATMENTS

[75] Inventors: John D. Travers, Yardley; Eileen C. Helzner, Plymouth Meeting, both of Pa.

[73] Assignee: Ethicon, Inc., Somerville, N.J.

[21] Appl. No.: 380,787

[22] Filed: Jan. 30, 1995

Related U.S. Application Data

[63] Continuation of Ser. No. 77,977, Jun. 15, 1993, abandoned.
[51] Int. Cl.⁶ .......................... A61K 31/19; A61K 31/195
[52] U.S. Cl. ............................................ 514/574; 514/562
[58] Field of Search ...................................... 514/574, 562

[56] References Cited

FOREIGN PATENT DOCUMENTS 1190856  7/1985  Canada ........................ A61K 31/185

OTHER PUBLICATIONS

Wanderlich et al. 97CA:207834y 1982.
Mihm et al. 115CA:174111a 1991.
Harakeh et al. 116 CA:50963a 1992.

*Primary Examiner*—Raymond Henley, III
*Assistant Examiner*—Russell Travens

[57]   ABSTRACT

A method for the prophylaxis or treatment of retroviruses in warm-blooded animals comprising administering to said warm-blooded animal a therapeutically effective amount of a dimercaptan acid, metabolites or pharmaceutically acceptable salts thereof alone or in combination with other drugs therapeutically effective in the treatment of said warm-blooded animal.

5 Claims, 4 Drawing Sheets

USE OF DIMERCAPTAN ACIDS, SALTS AND METABOLITES THEREOF AS ANTIRETROVIRAL TREATMENTS

This is a continuation of application Ser. No. 08/077,977, now abandoned, filed Jun. 15, 1993, which is hereby incorporated by reference.

FIELD OF INVENTION

The use of therapeutic amounts of dimercaptan acids, salts and metabolites thereof in warm blooded animals for the prophylaxis or treatment of retroviruses alone or in combination with other drugs.

BACKGROUND OF THE INVENTION

Meso-2,3 dimercaptosuccinic acid (DMSA), a dimercaptan acid is a heavy metal chelating or metal complexing agent that has been used extensively as a treatment of heavy metal poisoning for the past 30 years. In numerous animal studies, DMSA has been reported to be an effective heavy metal chelating agent for lead, mercury and arsenic. DMSA is favored as a treatment for heavy metal poisoning, because DMSA has been shown not to increase the excretion of essential minerals (calcium, magnesium, manganese, iron and zinc).

It has recently been discovered that meso-2,3 dimercaptosuccinic acid, its salts and metabolites can be used in warm-blooded animals for the prophylaxis or treatment of retroviruses.

SUMMARY OF INVENTION

In accordance with the present invention, we have discovered a method for the prophylaxis or treatment of retroviruses in warm blooded animals comprising administering to a therapeutically effective amount of a dimercaptan compound selected from the group consisting of meso-2,3 dimercaptosuccinic acid, metabolites of meso-2,3 dimercaptosuccinic acid and a pharmaceutically acceptable salt thereof alone or in combination with other drugs therapeutically effective in the treatment of said warm-blooded animal.

DETAILED DESCRIPTION OF THE INVENTION

Figure 1:
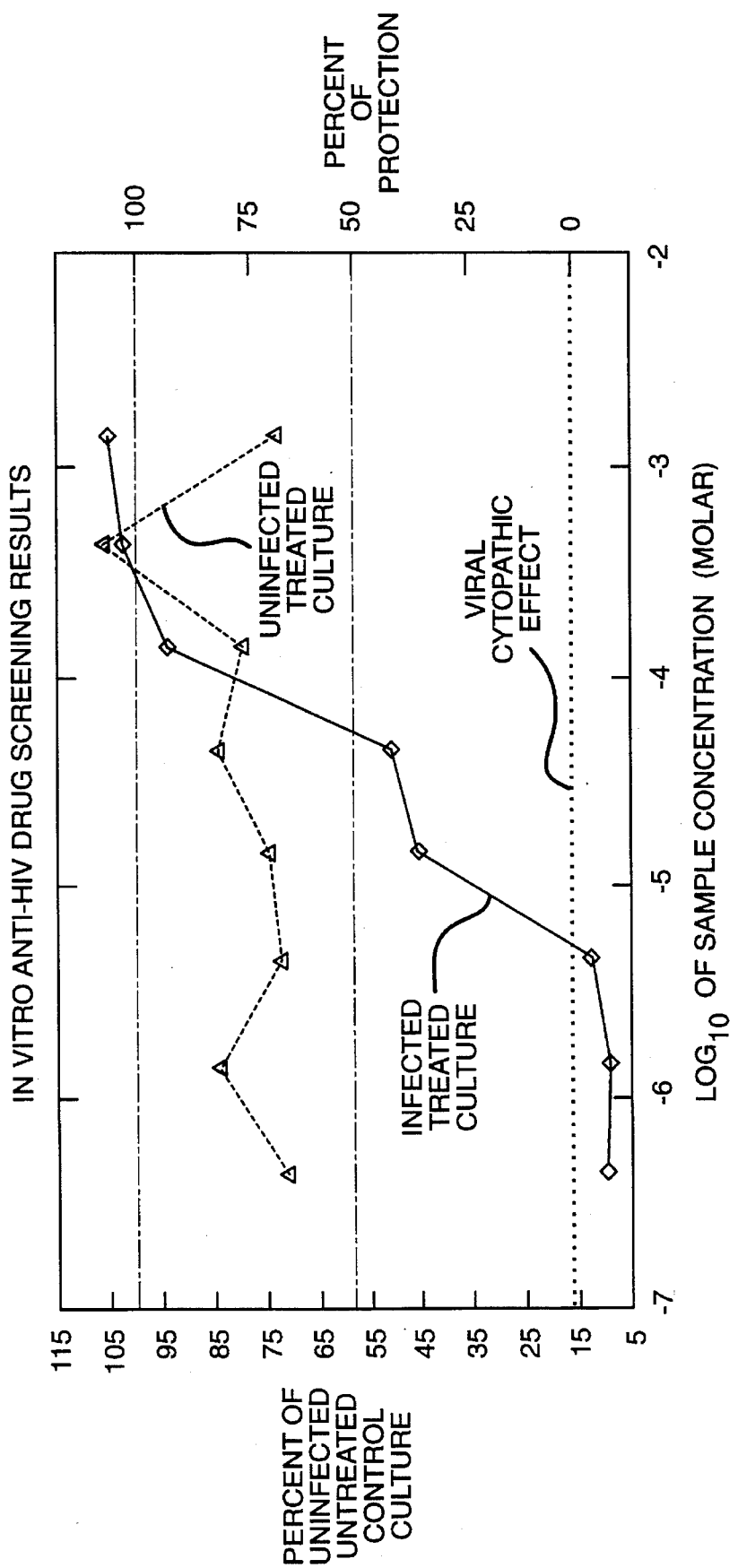
FIGS. 1–4 are plots of the $\log_{10}$ of the meso-2,3 dimercaptosuccinic acid concentrations (as moles/L or Molar) against the measured test values expressed as a percentage of the uninfected, untreated control values. The solid line connecting the diamond symbols depicts the percentage of surviving viral infected cells treated with sample (at the indicated concentration) relative to uninfected, untreated controls. This line expresses the in vitro anti-reteroviral activity of the meso-2,3 dimercaptosuccinic acid. The dashed line connecting the triangular symbols depicts the percentage of surviving uninfected cells treated with the meso-2,3 dimercaptosuccinic acid relative to the same uninfected, untreated controls. This line expresses the in vitro growth inhibitory properties of the meso-2,3 dimercaptosuccinic acid. The viral cytopathic effect in this particular experiment is indicated by a dotted reference line. This line shows the extent of destruction of cells by the virus in the absence of treatment and is used as a quality control parameter.

We have discovered as is shown in FIGS. 1-4 that certain dimercaptans may be used as a prophylaxis or treatment of retroviruses in warm-blooded animals. Suitable dimercaptan acids are described by formula below:

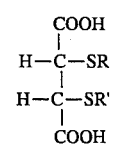

wherein R and R' are independently selected from the group consisting of hydrogen, a disulfide linkage to cysteine (—SCH$_2$CHNH$_2$COOH), a disulfide linkage to methionine, a disulfide linkage to glutathione and a disulfide linkage to 2,3, dimercaptosuccinic acid and pharmaceutically acceptable salts thereof. The most preferred mercaptan is meso-2,3 dimercaptosuccinic acid The compounds for formula I show antiretroviral properties. Until recently, retroviruses were considered to be the pathogenic agents in a number of non-human warm-blooded animal diseases only, unlike viruses which have been known for quite some time to be the cause of a large number of diseases in warm-blooded animals and humans alike. However, it has been established that a retrovirus infects humans.

Due to their antiretroviral properties, the compounds of formula I, their pharmaceutically acceptable salts and the stereochemically isomeric forms thereof, are useful in the treatment of warm-blooded animals infected with retroviruses or for the prophylaxis of said warm-blooded animals. The compounds of the present invention may be especially useful in the treatment of warm-blooded animals infected with retroviruses because these compounds may be used in conjunction with antiviral compounds such as nucleosides (including but not limited to 3'-azido-2',3' dideoxythymidine (AZT), 2',3'-dideoxyinosine (DDI), 2',3'-dideoxycytidine (DDC), 2',3'-dideoxyadenosine (DDA), 2',3'-dideoxy-2',3'-didehydrothymidine (D4T) and other reverse transcriptase inhibitors), glucosidase (including but not limited to N-butyldeoxynojirimycin) and anionic compounds (including but not limited to suramin and dextran sulphate).

In view of their antiretroviral activity, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspension, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. One suitable solid oral dosage form is described in Example 3. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims wherein refers to physically discrete units suitable as unitary dosages, each unit containing predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention provides a method of treating retroviral diseases in warm-blooded animals suffering from said retroviral diseases by administering an effective antiretroviral amount of a compound of formula (I), a pharmaceutically acceptable acid addition salt or a stereoisomeric form thereof. Those of skill in the treatment of viral diseases could easily determine the effective antiviral amount from the test results presented herein. In general it is contemplated that an effective amount would be from 20 mg/kg to 1000 mg/kg body weight and in particular from 40 mg/kg to 400 mg/kg body weight. It may be appropriate to administer the required dose as two, three, four or more sub-doses at appropriate intervals throughout the day. Said subdoses may be formulated as unit dosage form, for example, containing 5 to 1000 mg, preferably 5 to 500 mg and most preferably in dosage units 50 mg, 100 mg, 250 mg and 500 mg of active ingredient per unit dosage form.

The following examples are intended to illustrate and not to limit the invention in all its aspects. Unless otherwise stated, all parts therein are by weight.

EXAMPLE 1

This example describes a methodology suitable for assaying DMSA concentration bound and freely available in the blood plasma.

Determination of total DMSA and bound DMSA concentration

Reagents and Reference Standard

The following reagents and solutions were prepared for use in the assaying of DMSA content.

Dimercaptosuccinic Acid (DMSA) Working Reference Standard (WRS)

2-Mercaptonicotinic acid (2-MN)
Dithiothreitol (DTT) reagent grade
Monobromobimane (MBBr) reagent grade
Ammonium Phosphate dibasic, reagent grade $(NH_4)_2HPO_4$
Potassium phosphate dibasic, reagent grade $(K_2HPO_4$
Cetyltrimethylammonium Bromide (CATB)
Phosphoric acid 85%, reagent grade
Acetonitrile
Methanol
Methylene Chloride
Water, HPLC grade Solutions Phosphate Dibasic Solution 100 mM
Dissolve 17.41g of potassium phosphate dibasic in 1000 mL of water, mix well.

DMSA Stock Solution A (0.25 mg/ml)
Weigh accurately 25.0 mg DMSA WRS and transfer quantitatively into a 100 mL volumetric flask. Dissolve in and dilute to volume with Phosphate Dibasic Solution. Prepare fresh.

Diluted DMSA Solution B (0.05mg/mL)
Pipet 5.0 mL of DMSA Stock Solution A into a 25-mL volumetric flask, dilute to volume with Phosphate Dibasic Solution, mix well. Prepare fresh.

MBBr Stock Solution for BOUND DMSA (1.24 mg/mL)
Weigh accurately 31.0mg MBBr reagent grade and transfer quantitatively into a 25-mL volumetric flask. Dissolve in and dilute to volume with acetonitrile. Prepare fresh.

MBBR Stock Solution for TOTAL DMSA (1.24 mg/ml)
Weigh accurately 31.0mg MBBR reagent grade and transfer quantitatively into a 25-ml volumetric flask. Dissolve and dilute to volume with Phosphate Dibasic Solution. Prepare fresh.

2-MN Standard Stock Solution (0.025mg/mL)
Weigh accurately 25.0mg of 2-MN and transfer quantitatively into a 100
mL volumetric flask. Dissolve and dilute to volume with Phosphate dibasic solution, mix well. Pipet 25mL of this into a 50-mL volumetric, dilute to volume with Phosphate dibasic solution, mix well. This is the 2-MN Stock Standard. Prepare fresh.

Internal Standard Solution
Weigh accurately 10mg of DTT and transfer quantitatively into a 25-mL volumetric flask. Pipet 4.0mL of 2-MN stock solution. Dissolve and dilute to volume with Phosphate dibasic solution. Prepare fresh.

Mobile Phase (70:30)

(5mM CTAB, 20mM $(NH_4)_2HPO_2$ pH 6.5): Methanol Weigh 1.28g CTAB and 1.85g $(NH_2)_2HPO_4$ into 700 mL of water. Dissolve the solids and adjust the pH to 6.50 with 85% Phosphoric Acid. Add 300 mL of methanol, mix well and degas. Mobile phase composition may be adjusted to optimize chromatography. (Increasing composing of methanol will decrease the retention times.)

Standard Preparation

Note: It is necessary to prepare the standard sets fresh each day before doing sample preparation.

1. Into each of eight 25-mL volumetric flasks, pipet 20.0 mL of blank plasma.

2. According to the following table, pipet the appropriate amount of diluted DMSA Solution A or B into each respective flask and dilute to volume with Saline.

| Standard Conc (ug/mL) | Aliquot | DMSA Solution A or B |
|---|---|---|
| 30.0 | 3.0 | A |
| 25.0 | 2.5 | A |
| 20.0 | 2.0 | A |
| 15.0 | 1.5 | A |
| 10.0 | 1.0 | A |
| 4.0 | 2.0 | B |
| 2.0 | 1.0 | B |
| 0.0 | 0.0 | — |

Standard Preparation for Standard Validation

1. Pipet 1.0 mL of each standard into a borosilicate glass screw-top centrifuge tube.
2. Using an Eppendorf pipettor, add 1.0 mL of Internal Standard Solution to each of the above tubes, and cap tightly.
3. Vortex all tubes on a multivortexer for one minute.
4. Place the tubes in the dark for 30 minutes.
5. Using an Eppendorf pipettor add in the order given 1.0 mL Acetonitrile and 1.0 mL of MBBr Stock solution to each of the tubes and cap tightly. Multivortex the tubes for 30 seconds and place the tubes in the dark for 30 minutes.
6. Add 3.0 mL of methylene chloride to each tube, cap tightly. Vigorously shake each tube by hand for 10 second and centrifuge the tubes at 3000 RPM for 15 minutes.
7. Remove the top layer of the tube and place it into a separate, approximately labeled, borosilicate glass screw-top centrifuge tube. Add 3.0 mL of methylene chloride, cap tightly and shake vigorously each tube by hand for 10 seconds. Centrifuge the tubes at 3000 RPM for 15 minutes and place the top layer into a waters HPLC vial and inject onto a suitable HPLC.

Standard Validation by Statistical Analysis

Schedule duplicate injection for each standard concentration from 0.0 ug/mL to 30.0 ug/mL under appropriate method in Peakpro™. Upon completion of duplicate injections from each vial average the area counts and check the statistical parameters with an appropriate program.

Sample Preparation for BOUND DMSA

1. Blood samples should be drawn from each subject to be tested and will be spun down to provide plasma samples. These samples may be used immediately or frozen and thawed for later analysis. Frozen samples to be analyzed should be placed in a water bath not exceeding 45° C., and vortex for a few seconds, to allow solids to settle.
2. Pipet 1.0 mL of each sample into appropriately labeled borosilicate glass screw-top centrifuge tubes, using an Eppendorf pipet (or equivalent).
3. Using an Eppendorf pipet, add 1.0 mL of Internal Standard stock to each tube.
4. Cap tightly and vortex all tubes on a multivortexer for one minute.
5. Place the tubes in the dark for 30 minutes.
6. Using a Eppendorf piper, add in the order given 1.0 mL of acetonitrile and 1.0 mL of BOUND MBBr stock solution to each tube.
7. Cap tightly and vortex all tubes on a multivortexer for one minute.
8. Place the tubes in the dark for 30 minutes.
9. Add 3.0 mL of methylene chloride to each tube.
10. Cap each tube tightly and shake the tubes by hand for 20 seconds.
11. Centrifuge the tubes at 3000 RPM for 15 minutes.
12. Remove the top layer from each tubes and place it into a separate, appropriately labeled borosilicate glass screw-top centrifuge tube.
13. Add 3.0 mL of methylene chloride, cap tightly and shake vigorously by hand for 10 seconds. Centrifuge the tubes at 3000 RPM for 15 minutes. Place the top layer into a waters HPLC vial and inject onto a suitable HPLC.

Sample preparation for TOTAL DMSA

1. Draw 3-mL of blood from a patient and immediately add 3-mL of MBBr stock solution for TOTAL DMSA. Mix the sample well.
2. Spin the samples for 5 minutes and remove the supernatant. At this point the supernatant can be frozen.
3. If the samples are frozen, thaw the sample from each subject/treatment to be analyzed that day in a water bath not exceeding 45° C., and vortex for a few seconds Allow solids to settle.
4. Pipet 1.0 mL of each sample into an appropriately labeled borosilicate flask screw-top centrifuge tubes, using an Eppendorf pipet (or equivalent).
5. Using an Eppendorf pipet, add 1.0 mL of Internal Standard stock to each tube.
6. Cap tightly and vortex all tubes on a multivortexer for one minute.
7. Place the tubes in the dark for 30 minutes.
8. Using an Eppendorf piper add in the order given 1.0 mL of acetonitrile and 1.0 mL of BOUND MBBr stock solution into each tube.
9. Cap tightly and vortex all tubes on a multivortexer for one minute.
10. Add 3.0 mL of methylene chloride of each tube.
11. Cap each tube tightly and shake the tubes by hand or 10 seconds.
12. Centrifuge the tubes at 3000 RPM for 15 minutes.
13. Remove the top layer from each tubes and place it into a separate, appropriately labeled borosilicate glass screw-top centrifuge tube.
14. Ad 3.0 mL of methylene chloride, cap tightly and shake vigorously by hand for 10 seconds. Place the top layer into a waters HPLC vial and inject onto a suitable HPLC.

Autoinjector Tray Set-Up

Each standard set may be followed by about 20 samples.

Calculations

All samples are calculated against the standard curve using the appropriate program.

Interpretation of Data

Acceptability criteria for standard set is the same as noted previously. If the standard set fails, all samples must be rerun with a fresh standard set.

If any sample set shows abnormality in expected plasma concentration at any timepoint, the entire sample set must be rerun under a fresh standard set.

SUGGESTED CHROMATOGRAPHIC CONDITIONS (NOTE: Using an Ion Pairing mobile phase requires an hour of equilibration time before running. It is best to run at least one standard as a dummy file to optimize the PeakPro GC method before proceeding with any run.)

| | |
|---|---|
| Column: | 7.5 cm × 3.9 mm Waters NovaPak $C_{18}$ |
| Mobile: | 70:30 (5 mM CTAB, 20 mM $(NH_4)_2HPO_4$ pH 6.5: MEOH) |
| Detector: | Waters 490 |
| Range | 0.005 AUFS |
| Wavelength | 245 nm |
| Flow Rate: | 2.0 mL/min |
| Injection Volume: | 15 uL |
| # Injection/Vial | 2 |
| Approximate Retention Volumes: | DMSA: 5.9 minutes<br>2-MN: 15.0 minutes |

By periodically drawing blood samples from patients taking DMSA or its metabolites for the treatment of retoviral diseases the concentration of DMSA may be monitored in the patients body. By concomitantly monitoring the retroviral disease, doctors will be able to adjust the dosage of drug to provide the maximum beneficial dosage of DMSA or its metabolites.

cells, and a complete cycle of virus reproduction is necessary to obtain the required cell killing. Agents that interact with virions, cells, or virus gene-products to interfere with viral activities will protect cells from cytolysis. All tests are compared with at least one positive (e.g., AZT-treated) control done at the same time under identical conditions.

The Procedure

1. Dimercaptosuccinic acid was dissolved in dimethyl sulfoxide (unless otherwise instructed) then diluted 1:100 in cell culture medium before preparing serial half-$log_{10}$ dilutions. T4 lymphocytes (CEM cell line) were added and after a brief interval HIV-1 is added, resulting in a 1:200 final dilution of the compound. Uninfected cells with the compound serve as a toxicity control, and infected and uninfected cells without the compound serve as basic controls.
2. The cultures were incubated at 37° in a 5% carbon dioxide atmosphere for 6 days.
3. The tetrazolium salt, XTT, was added to all wells, and cultures were incubated to allow formazan color development by viable cells.
4. Individual wells were analyzed spectrophotometrically to quantitate formazan production, and in addition were viewed microscopically for detection of viable cells and confirmation of protective activity.
5. Drug-treated virus-infected cells were compared with drug-treated noninfected cells and with other appropriate controls (untreated infected and untreated noninfected cells, drug-containing wells without cells, etc.) on the same plate.
6. The data was reviewed in comparison with four other tests done at the same time and a determination about activity was made.

The Tabular Dose Response Data and Status Section provides a listing of the numerical data plotted in FIGS. 1–4. Approximate values to 50% effective concentration ($EC_{50}$), 50% inhibitory concentration ($IC_{50}$, and Therapeutic Index ($TI=IC_{50}/EC_{50}$) have been calculated for each test and are provided for your information. The determination of the activity of dimercaptosuccinic acid is printed in the lower left-hand corner.

The data from the tests is presented in Tables I–IV.

TABLE I

| SUMMARY | | DOSE | INFECTED RESPONSE | UNINFECTED RESPONSE |
|---|---|---|---|---|
| Index | Concentration | (Molar) | Percent of Control | Percent of Control |
| IC50 (Molar) | >1.40 × 10⁻³ | 4.40 × 10⁻⁷ | 9.56 | 71.13 |
| EC50 (Molar) | 5.30 × 10⁻⁵ | 1.40 × 10⁻⁶ | 8.92 | 84.21 |
| TI50 (IC/EC) | >2.60 × 10⁻¹ | 4.40 × 10⁻⁶ | 12.48 | 72.15 |
| Conclusion | | 1.40 × 10⁻⁵ | 45.85 | 74.62 |
| CONFIRMED ACTIVE | | 4.40 × 10⁻⁵ | 50.93 | 84.59 |
| | | 1.40 × 10⁻⁴ | 94.31 | 80.02 |
| | | 4.30 × 10⁻⁴ | 102.98 | 106.57 |
| | | 1.40 × 10⁻³ | 105.81 | 73.80 |

EXAMPLE 2

ANTI-HIV DRUG TESTING SYSTEM

The procedure used to test dimercaptosuccinic acid's activity against Human Immunodeficiency Virus (HIV) is the assay developed by Owen S. Weislow et al. described in "Journal of the National Cancer Institute," Vol. 81, No. 8, April 19, 1989 which is hereby incorporated herein by reference. The assay basically involves the killing of T4 lymphocytes by HIV. Small amounts of HIV are added to The data presented in Table I is graphically presented in FIG. 1.

TABLE II

| SUMMARY | | DOSE | INFECTED RESPONSE | UNINFECTED RESPONSE |
|---|---|---|---|---|
| Index | Concentration | (Molar) | Percent of Control | Percent of Control |
| IC50 (Molar) | $>1.40 \times 10^{-3}$ | $4.40 \times 10^{-7}$ | 6.12 | 86.80 |
| EC50 (Molar) | $6.50 \times 10^{-5}$ | $1.40 \times 10^{-6}$ | 7.73 | 87.16 |
| TI50 (IC/EC) | $>2.10 \times 10^{-1}$ | $4.40 \times 10^{-6}$ | 6.18 | 88.43 |
| Conclusion | | $1.40 \times 10^{-5}$ | 10.30 | 87.58 |
| CONFIRMED ACTIVE | | $4.40 \times 10^{-5}$ | 38.33 | 85.17 |
| | | $1.40 \times 10^{-4}$ | 84.32 | 81.43 |
| | | $4.30 \times 10^{-4}$ | 122.36 | 107.46 |
| | | $1.40 \times 10^{-3}$ | 119.78 | 106.56 |

Figure 2:
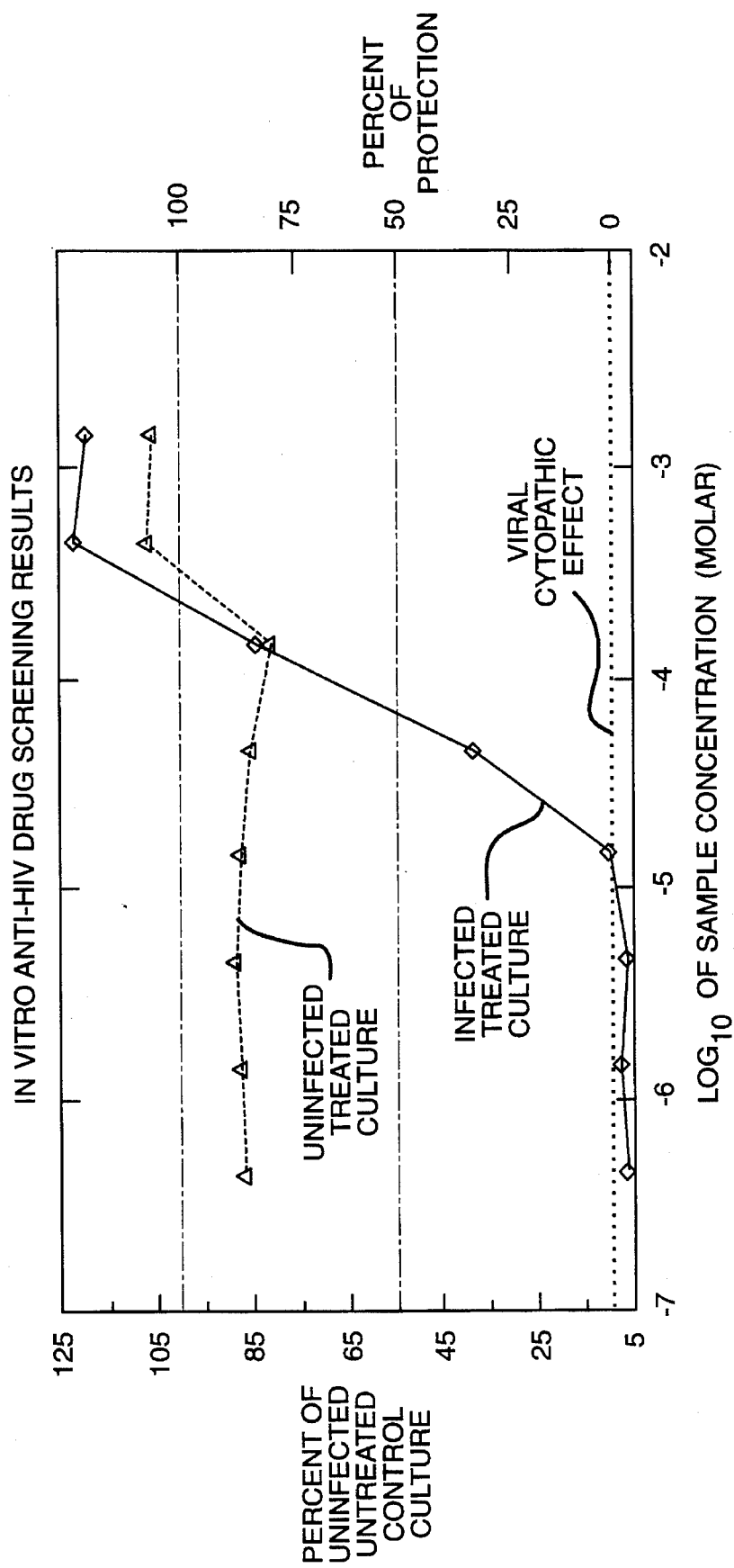

The data presented in Table II is graphically presented in FIG. 2.

TABLE III

| SUMMARY | | DOSE | INFECTED RESPONSE | UNINFECTED RESPONSE |
|---|---|---|---|---|
| Index | Concentration | (Molar) | Percent of Control | Percent of Control |
| IC50 (Molar) | $>1.40 \times 10^{-3}$ | $4.40 \times 10^{-7}$ | 4.20 | 148.54 |
| EC50 (Molar) | $2.40 \times 10^{-5}$ | $1.40 \times 10^{-6}$ | 5.89 | 106.99 |
| TI50 (IC/EC) | $>5.60 \times 10^{-1}$ | $4.40 \times 10^{-6}$ | 9.44 | 121.59 |
| Conclusion | | $1.40 \times 10^{-5}$ | 28.64 | 118.28 |
| CONFIRMED ACTIVE | | $4.40 \times 10^{-5}$ | 82.98 | 125.62 |
| | | $1.40 \times 10^{-4}$ | 103.60 | 107.87 |
| | | $4.30 \times 10^{-4}$ | 100.81 | 124.09 |
| | | $1.40 \times 10^{-3}$ | 97.63 | 115.22 |

Figure 3:
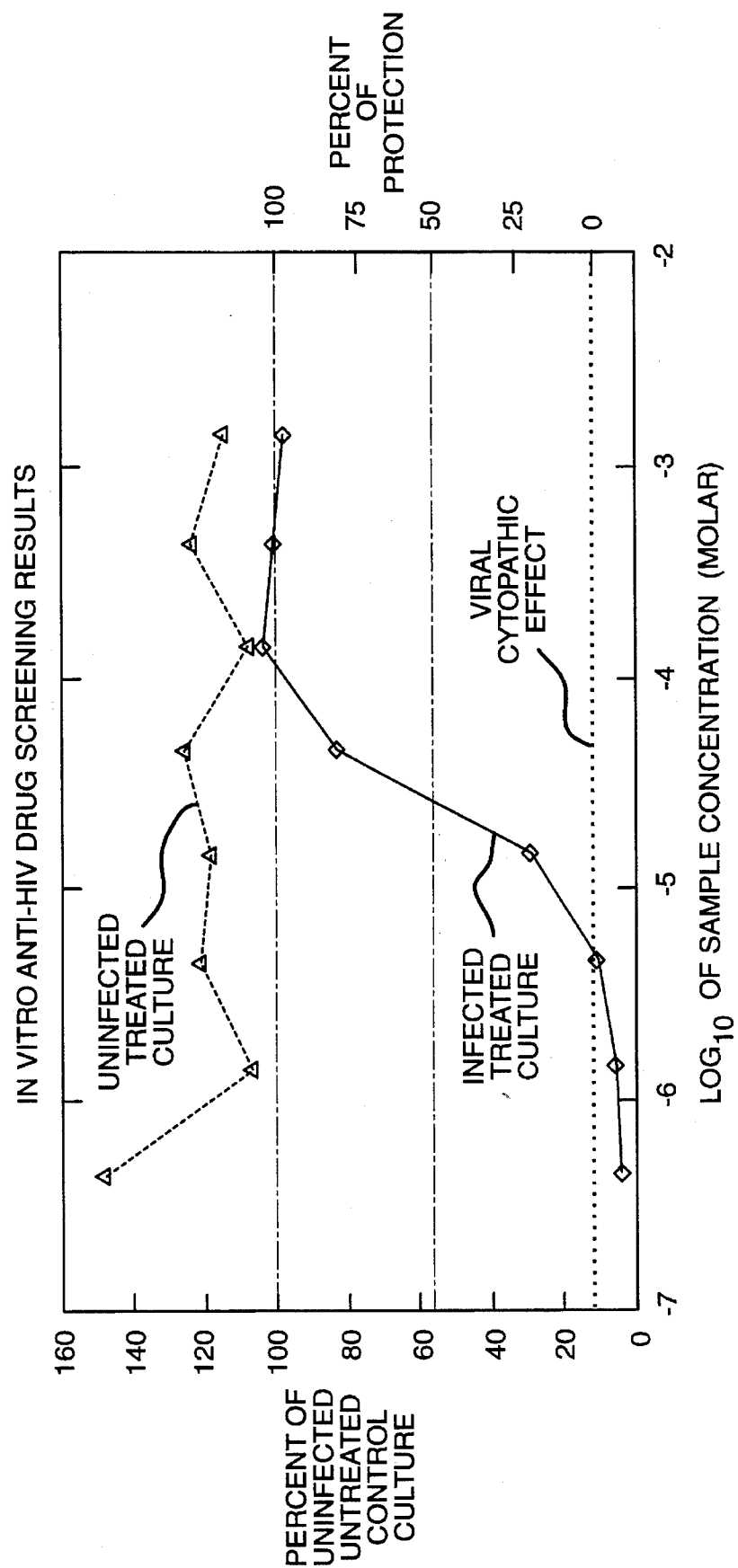

The data presented in Table III is graphically presented in FIG. 3.

TABLE IV

| SUMMARY | | DOSE | INFECTED RESPONSE | UNINFECTED RESPONSE |
|---|---|---|---|---|
| Index | Concentration | (Molar) | Percent of Control | Percent of Control |
| IC50 (Molar) | $>1.40 \times 10^{-3}$ | $4.40 \times 10^{-7}$ | 0.80 | 100.42 |
| EC50 (Molar) | $5.10 \times 10^{-5}$ | $1.40 \times 10^{-6}$ | 1.04 | 103.39 |
| TI50 (IC/EC) | $>2.70 \times 10^{-1}$ | $4.40 \times 10^{-6}$ | 1.24 | 101.46 |
| Conclusion | | $1.40 \times 10^{-5}$ | 12.27 | 102.83 |
| CONFIRMED ACTIVE | | $4.40 \times 10^{-5}$ | 43.91 | 102.99 |
| | | $1.40 \times 10^{-4}$ | 95.01 | 105.07 |
| | | $4.30 \times 10^{-4}$ | 99.10 | 128.49 |
| | | $1.40 \times 10^{-3}$ | 80.17 | 96.57 |

Figure 4:
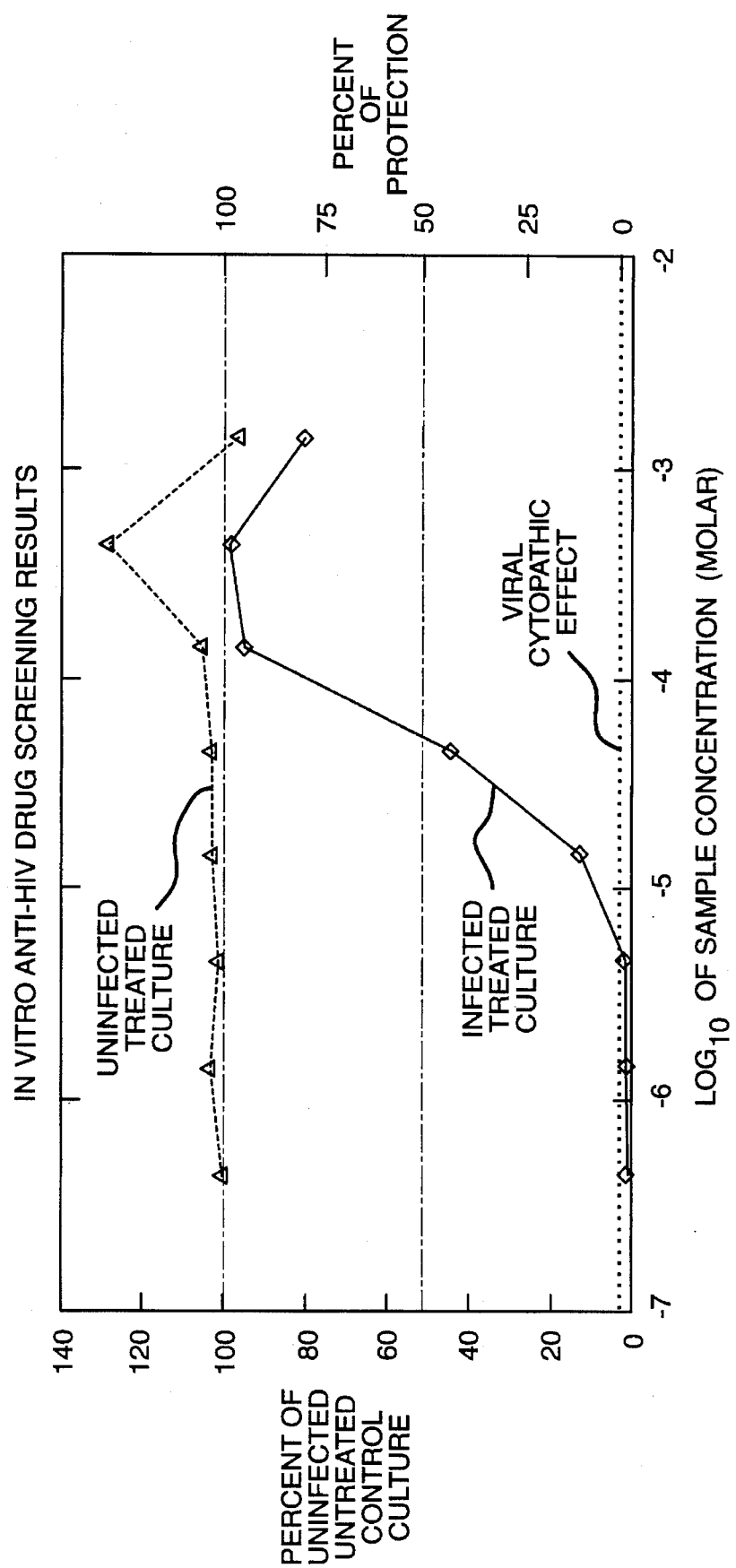

The data presented in Table IV is graphically presented in FIG. 4.

The data above clearly indicates that meso-2',3' dimeracptosuccinic acid is effective as a treatment for retroviruses in warm blooded animals when provided in a therapeutically effective dosage.

EXAMPLE 3

This Example describes one formulation for on oral dosage form containing 350 mg of meso-2,3 dimercaptosuccinic acid.

TABLE V

| Ingredients | mg per dosage unit |
|---|---|
| meso-2,3 Dimercaptosuccinic acid | 350.0 |

TABLE V-continued

| Ingredients | mg per dosage unit |
|---|---|
| Dextrates NF | 208.0 |
| Sodium Starch Glycolate NF | 24.0 |
| Hydrogenated Vegetable Oil NF | 18.0 |
| Empty Gelatin Capsule Shells | 99.6 |
| TOTAL | 699.6 mg |

The ingredients for this capsule were dry blended together in a twin shell blender until a homogeneous mixture was formed. The mixture was then loaded in a size 0 gelatin capsule using a H&K 330 capsule machine.

We claim:

1. A method for the treatment of retrovirus in humans comprising administering to a human infected with retrovirus a thereapeutically effective amount of a dimercaptan compound having the formula:

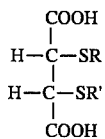

wherein R and R' are independently selected from the group consisting of hydrogen, a disulfide linkage to cysteine, a disulfide linkage to methionine, a disulfide linkage to gluthathione and a disulfide linkage to meso-2,3, dimercaptosuccinic acid and pharmaceutically acceptable salts thereof alone or in combination with other drugs thereapeutically effective in the treatment of said human.

2. The method of claim 1 wherein the mercaptan compound is meso- 2,3 dimercaptosuccinic acid.

3. The method of claim 2 wherein the therapeutically effective dosage is provided in a dosage form containing in the range of from 5 to 1000 mg per unit dosage form.

4. The method of claim 2 wherein the therapeutically effective dosage is provided in a dosage form containing in the range of from 5 to 500 mg per unit dosage form.

5. The method of claim 1 wherein the other drug is selected from the group consisting of 3'-azido-2',3' dideoxythymidine (AZT).

* * * * *